United States Patent [19]

Brannon

[11] Patent Number: 5,147,329

[45] Date of Patent: Sep. 15, 1992

[54] INTRAVENOUS ACCESS DEVICES

[76] Inventor: James K. Brannon, 5729 Canterbury Dr., Culver City, Calif. 90230

[21] Appl. No.: 727,372

[22] Filed: Jul. 5, 1991

Related U.S. Application Data

[63] Continuation of Ser. No. 270,400, Nov. 9, 1988, abandoned, which is a continuation-in-part of Ser. No. 13,417, Feb. 11, 1987, abandoned.

[51] Int. Cl.$^5$ .................. A61M 5/315; A61B 5/00
[52] U.S. Cl. .................. 604/231; 604/187; 604/239; 128/764; 128/765
[58] Field of Search .................. 604/36, 38, 164, 177, 604/184, 187, 205, 218, 226, 231, 236, 238, 239, 900; 128/760, 763–766, 770

[56] References Cited

U.S. PATENT DOCUMENTS

| 701,671 | 6/1902 | Billings | 604/218 |
|---|---|---|---|
| 1,272,742 | 7/1918 | Weguelin et al. | 604/226 |
| 1,410,530 | 3/1922 | Larche | 604/231 |
| 2,073,067 | 3/1937 | Klein et al. | 604/187 |
| 3,064,648 | 11/1962 | Bujan | 604/177 |
| 3,931,815 | 1/1976 | Takatsuki | 128/764 |
| 4,412,832 | 11/1983 | Kling et al. | 604/164 |
| 4,660,569 | 4/1987 | Etherington | 128/765 |
| 4,936,315 | 6/1990 | Lineback | 604/187 |

FOREIGN PATENT DOCUMENTS

| 0090782 | 1/1923 | Fed. Rep. of Germany | 604/164 |
|---|---|---|---|
| 3025800 | 2/1982 | Fed. Rep. of Germany | 128/765 |
| 0003778 | 6/1988 | PCT Int'l Appl. | 128/765 |

Primary Examiner—John D. Yasko
Assistant Examiner—Anthony Gutowski

[57] ABSTRACT

A disposable syringe for the dual extraction of a fluid for a plurality of vacuum glass tubes and other types of fluid reservoirs or alternately the delivery of an injectable fluid. A plunger of the syringe also functions as a conduit with one end thereof capable of sealably accepting a blood collection needle of a blood collection receptacle, and as such, allowing a fluid to flow from within the syringe, through said conduit, and into said plurality of vacuum glass tubes, without loss of the piston's ability to generate a positive or negative pressure within said syringe by advancing said plunger in a distal or proximal direction, respectively. Several embodiments of the plunger-conduit system are described.

18 Claims, 4 Drawing Sheets

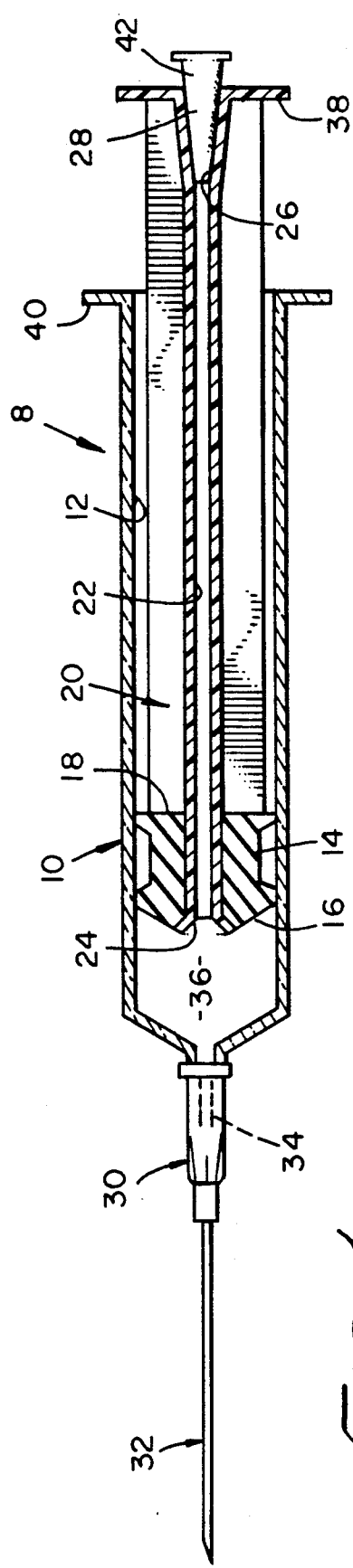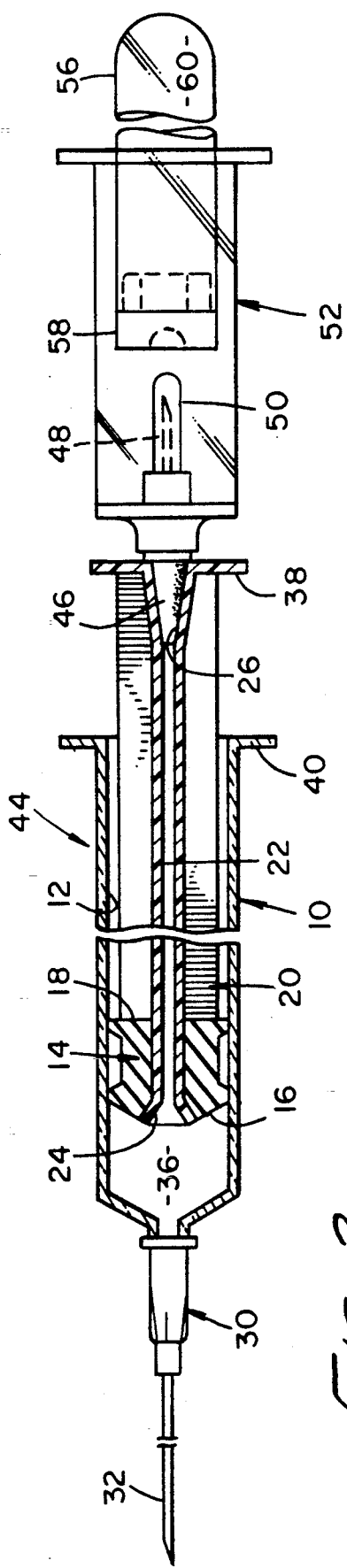

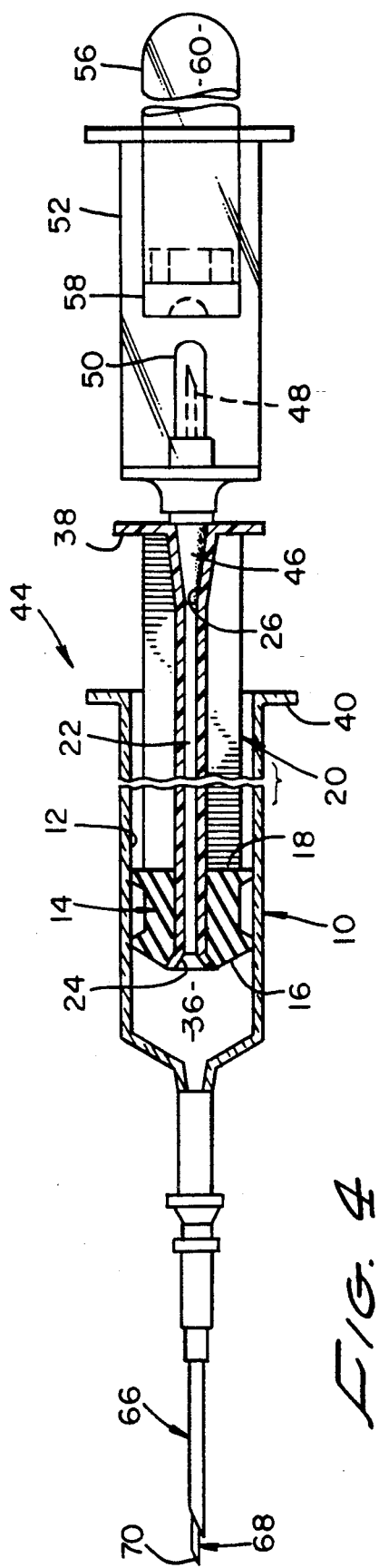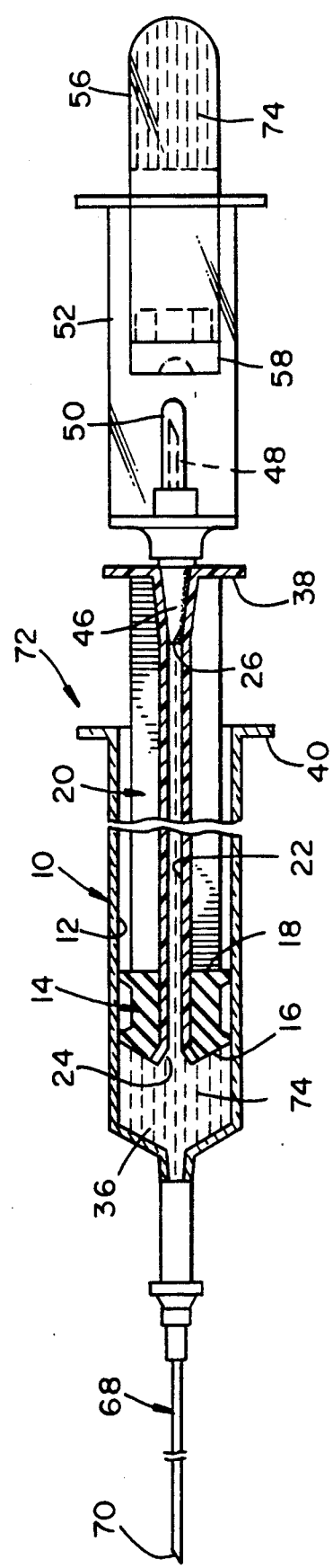

INTRAVENOUS ACCESS DEVICES

CROSS-REFERENCE TO RELATED APPLICATION

This application is a continuation of application Ser. No. 07/270,400 filed Nov. 9, 1988 (now abandoned), which is a continuation-in-part of U.S. application Ser. No. 07/013,417, filed Feb. 11, 1987, entitled "INTRAVENOUS ACCESS DEVICES" by James K. Brannon (now abandoned).

BACKGROUND OF THE INVENTION

1. Field of the Invention

This invention relates to a multipurpose syringe having a piston integral with a plunger-conduit system which may be attached to a blood collection receptacle alternately enabling use as a conventional syringe or a blood-fluid collection device, more specifically, a syringe for the hypodermic administration of drugs or other medicinal preparations or the collection of whole blood into a plurality of vacuum glass tubes housed within an attached said blood collection receptacle and concomitantly the collection of an additional volume of whole blood into said blood-fluid collection device from a single hypodermic site for the subsequent transfer of said additional volume of whole blood to a plurality of other types of blood reservoirs, such as blood culture vials.

2. Information Disclosure Statement

With the advent of the acquired immune deficiency syndrome (AIDS), it has become evident that patients with AIDS or other infectious diseases are often candidates for the collection of a plurality of blood samples, and while prior art has made numerous attempts to protect a user from accidental needle sticks, prior art devices means for facilitating a technique for the less cumbersome collection of said plurality of blood samples, and as such, an improved syringe apparatus is indicated.

Given that various medical procedures involve the percutaneous intravenous insertion of an intravenous catheter, a physician or technician will often concomitantly attempt to collect a sample of whole blood for appropriate testing. During the placement of an intravenous catheter, it is a common practice to place the intravenous catheter by use of a trocar extending through the catheter and distally beyond the catheter tip. The trocar carrying the catheter is inserted percutaneously into a patient's vein and the trocar then is removed leaving the catheter in place in the patient's vein. A syringe then is connected to the proximal end of the catheter and a volume of whole blood is drawn from the patient. The syringe then is detached from the intravenous catheter and is fitted with a needle so that the whole blood collected therein then may be injected into several vacuum glass tubes and blood culture vials, each tube and vial being intended for use in a different test. The foregoing procedure involves numerous steps, is time consuming and is cumbersome. Additionally, the physician or technician is often unable to collect a sufficient volume of whole blood for the number of blood test indicated. And when a larger volume syringe is attached to the intravenous catheter as means for obtaining a sufficient volume of whole blood, the patient's vein often collapses, prior to the collection of a sufficient volume of whole blood, because the larger syringe generates too great of a negative pressure for the patient's vein to withstand. Yet further, if the patient's vein does not collapse, the procedure still remains time consuming in addition to the inevitable threat of an accidental needle stick while injecting the collected whole blood into the vacuum glass tubes.

Various other medical procedures involve the percutaneous intravenous insertion of a hypodermic needle for purposes of simultaneously collecting whole blood for vacuum glass tubes and blood culture vials. During such procedures, it is a common practice to first attach a syringe to a hypodermic needle and subsequently, the needle is percutaneously placed into the patient's vein. Whole blood then may be drawn within the syringe and subsequently injected into vacuum glass tubes and blood culture vials. This procedure too is fraught with the problems described above. In an effort to alleviate the problems associated with this procedure, a Butterfly needle or a hypodermic needle is directly attached to a blood collection receptacle, and in so doing, a plurality of vacuum glass tubes may be filled. Then thereafter, said blood collection receptacle is detached from said Butterfly needle or said hypodermic needle, and with said Butterfly needle or said hypodermic needle still remaining in the patient's vein, a syringe is attached thereto and an additional volume of whole blood may be obtained for blood culture vials. However, this procedure is fraught with many manipulations and increases patient anxiety because of the continuous distal and proximal movement of the needles during the required attaching and detaching of the devices described, as well as that movement of the needles required to ensure that the tips thereof have remained within the lumen of the patient's vein. Yet further, because blood flow through the respective needle is not continuous, the blood therein has a tendency to clot, thereby further complicating the procedure. Yet even further, if the physician chooses to stick the patient twice, the patient by necessity must have another peripheral venous access site, and again, patient anxiety is unduly increased.

Various other medical procedures involve the percutaneous intravenous insertion of a trocar into the subclavian or internal jugular veins for purposes of central venous catheterization. This catheterization procedure is often indicated on patients requiring large volumes of fluid. Additionally, many of these patients require numerous blood test. And as such, during the placement the trocar, it is a common practice to attach a syringe to the trocar and subsequently, the trocar is percutaneously inserted into the patient's subclavian or internal jugular vein. Whole blood then may be drawn into the syringe in the usual fashion and subsequently transferred to a plurality of vacuum glass tubes. Although the physician may obtain a sufficient volume of whole blood and does not worry about collapse of the patient's large central vein, the subsequent transfer of the collected whole blood to vacuum glass tubes remains a time consuming and cumbersome procedure. Additionally, the physician is at an increased risk for an accidental needle stick.

Various other medical procedures involve the percutaneous intravenous insertion of a double tip hollow needle attached to a blood collection receptacle, with one end of said double tip hollow needle extending within said blood collection receptacle and the opposite end extending distally away from said blood collection receptacle, for purposes of obtaining a plurality of whole blood samples. With the distal end of the needle in place in the patient's vein, a plurality of vacuum glass tubes are inserted into the proximal end of said blood collection receptacle and said plurality of whole blood samples are obtained. This procedure is often fraught with difficulties when attempted on obese, elderly, and pediatric patients, as well as intravenous drug abusers, all of which in hereinafter referred to as patients with poor peripheral access. The problems include loss of the negative pressure within said vacuum glass tubes because of continuous proximal and distal motion as means to access the patient's vein, as well as increased physician or technician and patient anxiety. In an effort to alleviate these problems, it is a common practice to attach a small gauge Butterfly needle to a syringe and subsequently percutaneously insert the needle into the patient's vein. Whole blood then may be withdrawn into the syringe and subsequently injected into said plurality of vacuum glass tubes. This procedure is also fraught with the problems noted above and these problems are exacerbated when attempted on a patient with poor peripheral access.

Various other medical procedures involve the percutaneous insertion of a hypodermic needle into the pleural space of a patient with a fluid collection around the lungs. It is a common practice to use a thoracentesis-tray for this procedure when fluid surrounding the lungs is to be removed for both therapeutic and diagnostic purposes. However, if the fluid is to be removed for diagnostic purposes only, a syringe with a hypodermic needle attached thereto is used instead of the thoracentesis-tray. The hypodermic needle is percutaneously inserted into the pleural space, fluid is withdrawn into the syringe and some but not all of the fluid is injected into a plurality of vacuum glass tubes, the remaining fluid being intended for a different kind of test. Therefore, when a thoracentesis is performed for diagnostic purposes only, it too is fraught with the problems noted above; time consuming and cumbersome manipulations, and an increased risk of an accidental needle stick.

In view of the numerous aforementioned problems, the objectives of the present invention are set forth and described herein.

In preparation for this application a review was conducted of patents in Classes 128 and 604, subclasses 764, and 164, 168, 198, respectively. In contradistinction to the patent application at hand, U.S. Pat. No. 4,676,783 of Jagger et. al., Class 604, subclass 198 teaches an outer tube which does not function as a fluid conduit and a flexible inner tube with a function readily distinguishable from that which follows.

SUMMARY AND OBJECTS OF THE INVENTION

It is an object of the present invention to provide an improved disposable syringe which incorporates a plunger conduit-system that facilitates both percutaneous injection of drugs or other medicinal preparations, or alternately the collection of a fluid into a plurality of vacuum glass tubes concomitantly with the collection of an additional volume of fluid into the barrel of the syringe.

It is a further object of the invention to provide such a syringe with a piston integral with a plunger having a conduit with an open funnel-mouth distal end and an open funnel-shaped proximal end, with said conduit extending distally completely through, but not beyond, said piston and proximally completely through said plunger, with said conduit having a uniformly constant internal diameter throughout said plunger and said piston, except at the open funnel-shaped proximal end and the open funnel-mouth distal end, with the proximal end of said conduit capable of sealably accepting the blunt end of a blood collection needle or a plug capable of being detached.

It is a yet further object of the invention to provide such a syringe with a piston capable of generating a negative pressure within the syringe barrel distal to said piston when the plunger-conduit system in advanced proximally, and a positive pressure within the barrel of the syringe distal to said piston when the plunger-conduit system is advanced distally when the proximal of the conduit is completely sealed off.

It is a feature of the present invention to facilitate fluid collection for a plurality of vacuum glass tubes concomitant with fluid collection for a plurality of other fluid reservoirs from an intravenous site, simultaneous with intravenous catheter placement, both peripherally and centrally.

It is yet another feature of the invention to facilitate the simultaneous collection of a sufficient volume of whole blood for a plurality of vacuum glass tubes and a plurality of blood culture vials without having to use a Butterfly needle or a hypodermic needle directly attached to a blood collection receptacle as described herein.

It is yet another feature of the invention to facilitate the collection of whole blood from patients with poor peripheral access in a less cumbersome and less time consuming manner, without needlessly wasting vacuum glass tubes and unduly increasing patient anxiety.

It is yet another feature of the invention to facilitate a less cumbersome diagnostic thoracentesis.

It is yet another feature of the invention to reduce the health care provider's risk of an accidental needle stick.

It is yet another feature of the invention to facilitate less anxiety in the patient because the aforementioned procedures can be performed in a less cumbersome and less time consuming manner, which is cost effective, safe, simple, and efficient.

SUMMARY

The invention describes a disposable syringe for the delivery of an injectable fluid or alternately the collection of whole blood for a plurality of vacuum glass tubes or other fluid reservoirs having a piston integral with a plunger having a conduit located centrally therewithin said plunger, with said conduit extending distally completely through, but not beyond, said piston and proximally completely through said plunger, and said conduit has an open funnel-mouth distal end and an open funnel-shaped proximal end capable of sealably accepting a blood collection receptacle or a plug capable of being detached therefrom.

When the plunger-conduit system is sealed off with the detachable plug, no air or fluid can enter the barrel of the syringe distal the piston via the conduit. Therefore, the plunger-conduit system serves as a plunger and enables use of the invention as a conventional syringe. However, when the detachable plug is removed from the proximal end of the plunger-conduit system, and the blunt end of a blood collection needle with a rubber sleeve housed over its needle portion is attached thereto, the plunger-conduit system serves as a potential conduit enabling use of the invention as a multipurpose syringe. Thus, with said blood collection needle attached to the plunger-conduit system, an air-fluid proof seal is established and as such, no air or fluid can enter the barrel of the syringe distal to the piston via the conduit. Therefore, when the plunger-conduit system is advanced in a proximal direction, a negative pressure is generated within the barrel of the syringe distal to the piston and a fluid can be drawn therewithin, and conversely, if the plunger-conduit system is advanced in a distal direction, a positive pressure is generated within the barrel of the syringe distal to the piston and said fluid can be expressed therefrom. Yet further, if a vacuum glass tube is inserted into the proximal end of a blood collection receptacle attached to said blood collection needle, a fluid can be drawn through the barrel of the syringe, the piston, the conduit, and into said vacuum glass tube, and after removal of said vacuum glass tube, the air-fluid proof seal is re-established and a negative or positive pressure can be re-generated within the barrel of the syringe distal to the piston as described herein. Therefore, a fluid collected into the barrel of the syringe distal to the piston, after a plurality of vacuum glass tubes have been filled, may be injected into other fluid reservoirs, such as blood culture vials.

Further objects and features of the invention will become apparent after reviewing the description of the embodiments together with the drawings which follow.

BRIEF DESCRIPTION OF THE DRAWINGS

FIG. 1 is a sectional view of the syringe of this invention with the piston withdrawn and the detachable plug attached to the proximal end of the plunger-conduit system ready for injection;

FIG. 2 is a sectional view of the syringe of this invention with the piston withdrawn and a blood collection receptacle attached to the proximal end of the plunger-conduit system ready for use on a patient with good peripheral access whom requires the collection of whole blood for a plurality of vacuum glass tubes concomitant with the collection of whole blood for a plurality of blood culture vials, and additionally, the arrangement shown may be used to perform a diagnostic thoracentesis;

FIG. 4 is a sectional view of the syringe of FIG. 2, but shown with an intravenous catheter attached ready for use on a patient whom requires intravenous catheter placement concomitant with the collection of whole blood for a plurality of vacuum glass tubes and a plurality of blood culture vials;

FIG. 5 is a sectional view of the syringe of FIG. 4, but shown with the trocar still attached and whole blood within the barrel of the syringe, the conduit, and the vacuum glass tube;

DESCRIPTION OF THE PREFERRED EMBODIMENTS

Figure 3:
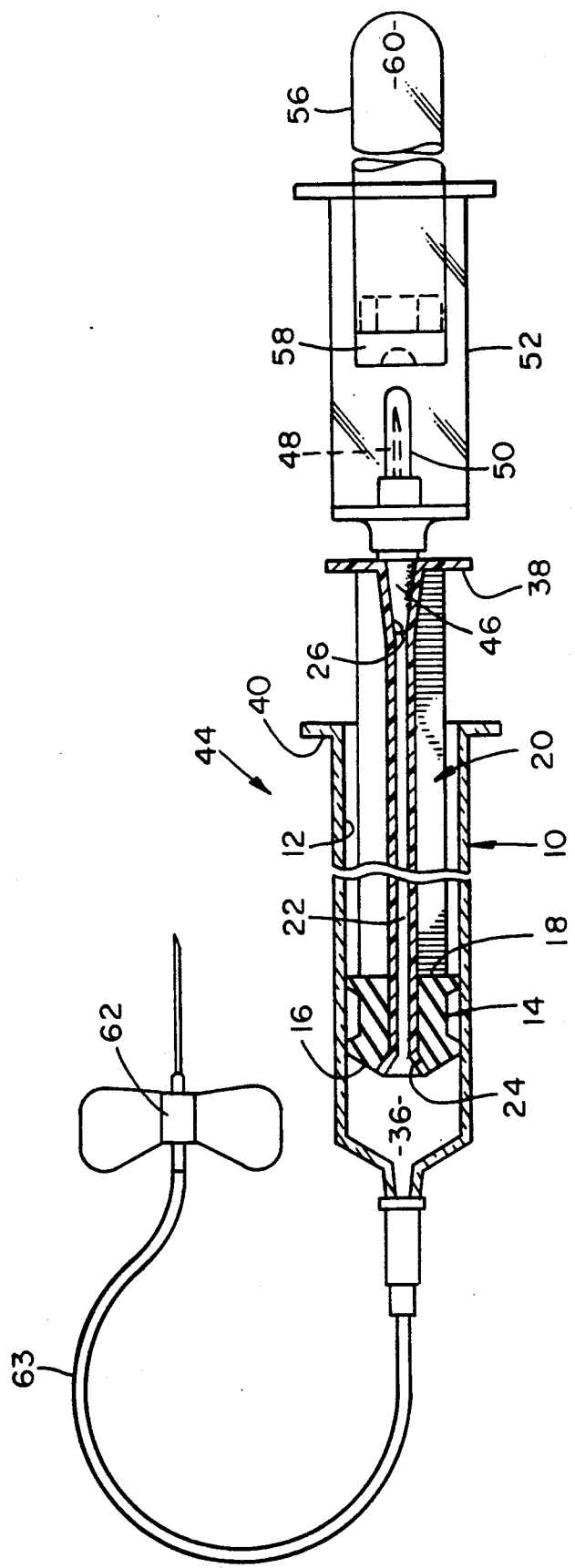
FIG. 3 is a sectional view of the syringe of FIG. 2, but shown with a Butterfly needle attached ready for use on a patient with poor peripheral access whom requires the collection whole blood for a plurality of vacuum glass tubes.

Referring now to FIG. 1, there is shown generally at 8 an improved disposable syringe of the present invention which comprises a cylindrical body or barrel 10. In syringes of this variety, it is common for the cylindrical body to be manufactured from a transparent or substantially transparent material so that injectable fluids therein can be visually monitored. At one end of the cylindrical body 10 a hub 30 is detachable, yet securely mounted. A cannula or hypodermic needle 32 is attached to the hub 30, and in the operative position extends away from the cylindrical body 10, which for descriptive purposes in hereinafter termed the distal end of the syringe. This assemblage establishes a complete closure, typical of a conventional syringe, except for a passageway 34 permitting fluids to flow between the interior of the cylindrical body and the interior of the hypodermic needle. In the other end of the cylindrical body 10, a piston 14 is fitted which provides a fluid seal at the juncture thereof and the interior wall 12 of the cylindrical body 10. Now further describing the piston 14 when positioned within the cylindrical body 10, the piston has two faces, one adjacent the distal end or fluid-chamber face 16 and the proximal face or plunger mounting face 18 to which a plunger 20 is mounted. Now further describing the plunger 20 when fitted to the piston 14, the plunger 20 has a conduit 22 which extends in a central position distally completely through the piston 14, but not beyond, having an open funnel-mouth 24, and said conduit 22 extends in a central position proximally completely through the plunger 20 having an open funnel-shaped end 26. The funnel-shaped end 26 is capable of sealably accepting a plug 28 which is capable of being detached. When the plug 28 is sealably positioned in the funnel-shaped end 26, no fluid or air can pass through the conduit 22 and the assemblage substantially closes one end of the conduit which for descriptive purposes in hereinafter termed the proximal end of the conduit 22. When the piston is fitted to the interior wall of the cylindrical body and the plunger is mounted to the proximal face of the piston with the proximal end of the conduit sealably closed with the plug, a fluid chamber 36 is defined bounded by the interior wall of the cylindrical body, the distal end of the cylindrical body, and the fluid-chamber face of the piston. The plunger 20 is constructed so as to fit loosely therewithin the interior wall 12 of the cylindrical body 10, yet preventing substantial lateral motion of the plunger 20, and to extend proximally beyond the mouth of the cylindrical body 10 including at the proximal end thereof a platform 38 to facilitate the operation of the syringe. In cooperative functional relationship therewith, the cylindrical body 10 is constructed with a finger rest 40, and the plug 28 is constructed with a thumb rest 42. Now with the syringe as shown, the second and third fingers may be placed on the finger rest 40 and the thumb on the thumb rest 42 and in this manner a fluid can be expelled by advancing the plunger 20 in a distal direction.

Referring now to FIG. 2, there shown generally at 44 is the multipurpose syringe of this invention with a blunt end 46 of a blood collection needle 48 sealably attached to the funnel-shaped end 26 of the conduit 22. It is common for blunted blood collection needles of this variety to consist of a rubber sleeve 50. The needle 48 with the blunt end 46 is fitted to a blood collection receptacle 52. With the rubber sleeve 50 advanced beyond the tip of the needle 48 as shown, and the blunt end 46 of the needle positioned in the funnel-shaped end of the conduit, the established seal is complete and no air or fluid can enter the conduit 22 via the funnel-mouth 24 or the funnel-shaped end 26 while advancing the piston 14 in a proximal or a distal direction. Therefore, the hypodermic needle 32 may be percutaneously inserted into a patient's vein or the pleural cavity surrounding the lungs and in so doing, whole blood or fluid can be drawn within the fluid chamber 36 adjacent the piston face 16 by advancing the piston 14 in a proximal direction. After percutaneous insertion of the hypodermic needle 32 into a patient's vein or pleural cavity whole blood or fluid can be observed within the fluid chamber 36 by advancing the piston 14 proximally, then thereafter, a vacuumed glass tube 56 may be inserted into the proximal end of the blood collection receptacle 52. In an uncomplicated manner, the needle 48 pierces the rubber sleeve 50 and a rubber stopper 58 of the vacuum glass tube 56, and in so doing, an interior chamber 60 of the vacuum glass tube freely communicates with the conduit 22 having the funnel mouth 24 which facilitates the influx of fluid therethrough. After removal of the vacuum glass tube from the blood collection receptacle, the rubber sleeve re-advances over the needle 48 once again making the seal complete. Therefore, and additional volume of whole blood or fluid, not intended for a plurality of vacuum glass tubes, can be obtained by advancing the piston 14 in a proximal direction.

Referring now to FIG. 3, there shown generally at 44 is the syringe of FIG. 2, but shown with a Butterfly needle 62 having a proximal tubing 63 mounted to the distal end of the cylindrical body 10. The assemblage as shown is for use on patients with poor peripheral access. Therefore, the Butterfly needle 62 is percutaneously inserted into the patient's vein, then thereafter, the piston 14 is advanced proximally using a substantially gentle force so as not to generate a substantial negative pressure within the fluid chamber 36 of the cylindrical body 10. In so doing, whole blood can be withdrawn into the fluid chamber 36, then thereafter, the whole blood can be collected into a vacuum glass tube 56 by inserting said vacuum glass tube 56 into the proximal end of the blood collection receptacle 52. If a plurality of vacuum glass tubes is required, the procedure may simply be repeated as described herein.

Referring now to FIG. 4, there shown generally at 44 is the syringe of FIGS. 2 and 3, but with an intravenous catheter 66 mounted onto a peripheral venous trocar 68 attached to the distal end of the cylindrical body 10. During use of this assemblage, the peripheral venous trocar tip 70 is percutaneously inserted into the patient's vein and whole blood then can be drawn therewithin and into the fluid chamber 36 by advancing the piston 14 in a proximal direction. Thereafter, the vacuum glass tube 56 may be inserted into the proximal end of the blood collection receptacle 52 and whole blood can be collected into a plurality of vacuum glass tubes as described herein. Yet further, as described herein, an additional volume of whole blood, not intended for vacuum glass tubes, can be drawn into the fluid chamber 36 by advancing the piston 14 in a proximal direction. Thereafter, the intravenous catheter 66 may be threaded into the patient's vein as the procedure dictates.

Referring now to FIG. 5, there shown generally at 72 is the syringe of FIGS. 2, 3, and 4, but shown after the intravenous catheter 66 has been placed in the patient's vein and the peripheral venous trocar 68 remaining attached to the distal end of the cylindrical body 10. Observed is whole blood 74 within the fluid chamber 36, the conduit 22 with the funnel-mouth 24, and the vacuumed glass tube 56. As described herein, the rubber sleeve 50 has re-advanced over the blood collection needle 48, and in so doing, the re-established seal of the proximal end of the conduit 22 is complete. Therefore, the whole blood 74 can be expelled through the distal end of the cylindrical body 10 and not the proximal end of the conduit 22 into blood reservoirs other than vacuumed glass tubes.

Figure 6:
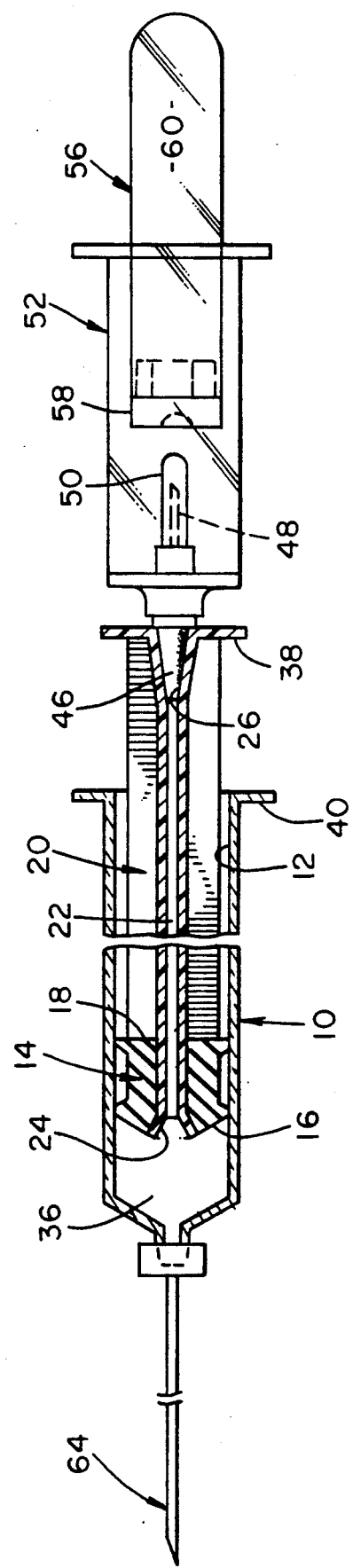
FIG. 6 is a sectional view of the syringe of FIG. 2, but shown with a central intravenous catheter trocar attached ready for use on a patient requiring central venous catheterization concomitant with the collection of whole blood for a plurality of vacuumed glass tubes.

Referring now to FIG. 6, there shown generally at 44 is the syringe of FIGS. 2, 3, and 4, but shown with a central venous trocar 64 attached to the distal end of the cylindrical body 10. During use of this assemblage, the central venous trocar 64 is percutaneously inserted into the patient's right lateral neck region and advanced toward the internal jugular vein. With one hand on the cylindrical body 10, second and third fingers of the other hand on the platform 38, and the funnel-shaped end 26 of the conduit 22 sealed off with the blood collection needle as described herein, the piston 14 can be advanced in a proximal direction by applying a proximal force thereto, thereby generating a negative pressure therewithin the fluid chamber 36 simultaneous with distal advancement of the central venous trocar 64 towards the patient's internal jugular vein. After whole blood is observed in the fluid chamber 36, a plurality of vacuumed glass tubes can be filled as described herein, and subsequently, an additional volume of whole blood can be obtained, not intended for vacuumed glass tubes, by advancing the piston in a proximal direction. Thereafter, the multipurpose syringe can be detached from the central venous trocar, leaving the trocar in the patient's vein, and central venous catheterization may proceed as the procedure dictates.

It should be understood that the foregoing description of the invention is intended merely to be illustrative thereof and that other modifications and embodiments may be apparent to those skilled in the art without departing from its spirit.

Having thus described the invention what I desire to claim and secure by letters patent is:

1. A syringe for extraction of a fluid into at least one fluid container or for delivery of an injectable fluid comprising:

(a) a cylindrical body having a distal end and an open proximal end, said distal end including an opening and a portion of a size and shape adapted for mounting a cannula thereon, said distal end being open to the flow of fluids into and out of said cylindrical body through said opening at all times when said syringe is in use;

(b) a piston sealably engaging, and slidable along the interior wall of said cylindrical body, said piston including a piston face extending transversely across said interior wall and defining a fluid chamber between said piston face and said distal end of said cylindrical body;

(c) plunger means for moving said piston proximally or distally within said cylindrical body, said plunger means being attached at one end to said piston, said plunger means having another end extending beyond said open proximal end of said cylindrical body, said plunger means having a size and shape that minimizes substantial lateral motion in said cylindrical body;

(d) conduit means extending distally through said piston and proximally through said plunger means, said conduit means having a sufficiently narrow, uniform internal diameter to induce the passage of a fluid into said fluid chamber and through said piston and said plunger means; and (e) detachably engaging the proximal end of said conduit means, means for sealing said proximal end of said conduit means to the inflow and outflow of air to said conduit means, said sealing means comprising a fluid collection receptacle sealably engaging said open proximal end of said conduit means, said fluid collection receptacle including a passage that communicates with the interior of said conduit means.

2. A syringe as defined in claim 1 wherein said conduit means includes a funnel-mouth distal end in said piston face.

3. A syringe as defined in claim 1 wherein said proximal end of said conduit means has a size and shape adapted to sealably engage said sealing means.

4. A syringe as defined in claim 1 further comprising a funnel-shaped portion at said open proximal end of said conduit means.

5. A syringe as defined in claim 1 further comprising, mounted within said passage, needle means extending into said receptacle, and sleeve means sealably covering said needle means.

6. A syringe as defined in claim 5 further comprising a butterfly needle affixed to said distal end portion.

7. A syringe as defined in claim 5 further comprising a venous trocar with an intravenous catheter over said venous trocar affixed to said distal end portion.

8. A syringe as defined in claim 1 further comprising a butterfly needle affixed to said distal end portion.

9. A syringe as defined in claim 1 further comprising a venous trocar with an intravenous catheter over said venous trocar affixed to said distal end portion.

10. A syringe as defined in claim 1 further comprising, affixed to said distal end portion, a needle adapted to obtain a blood sample from a patient with poor peripheral access for obtaining said sample through said needle.

11. A syringe for extraction of a fluid into at blast one fluid container or for delivery of an injectable fluid comprising:

(a) a cylindrical body having a distal end and an open proximal end, said distal end including an opening and a portion of a size and shape adapted for mounting a cannula thereon, said distal end being open to the flow of fluids into and out of said cylindrical body through said opening at all times when said syringe is in use;

(b) plunger means having piston means at one end of said plunger means, said piston means sealably engaging, and slidable along the interior wall of said cylindrical body, said piston means including a portion extending transversely across said interior wall and defining a fluid chamber between said piston means and said distal end of said cylindrical body, said plunger means being adapted for moving said piston means proximally or distally within said cylindrical body, said plunger means having another end extending beyond said open proximal end of said cylindrical body, said plunger means having a size and shape that minimizes substantial lateral motion in said cylindrical body;

(c) conduit means extending distally through said piston means and proximally through said plunger means, said conduit means having a sufficiently narrow, uniform internal diameter to induce the passage of a fluid into said fluid chamber and through said piston and said plunger means; and (d) detachably engaging the proximal end of said conduit means, means for sealing said proximal end of said conduit means to the inflow and outflow of air to said conduit means, said sealing means comprising a fluid collection receptacle sealably engaging said open proximal end of said conduit means, said fluid collection receptacle including a passage that communicates with the interior of said conduit means.

12. A syringe as defined in claim 11 further comprising, mounted within said passage, needle means extending into said receptacle, and sleeve means sealably covering said needle means.

13. A syringe as defined in claim 12 further comprising a butterfly needle affixed to said distal end portion.

14. A syringe as defined in claim 12 further comprising a venous trocar with an intravenous catheter over said venous trocar affixed to said distal end portion.

15. A syringe as defined in claim 11 further comprising a butterfly needle affixed to said distal end portion.

16. A syringe as defined in claim 11 further comprising a venous trocar with an intravenous catheter over said venous trocar affixed to said distal end portion.

17. A syringe as defined in claim 11 further comprising, affixed to said distal end portion, a needle adapted to obtain a blood sample from a patient with poor peripheral access for obtaining said sample through said needle.

18. A syringe as defined in claim 5 further comprising, affixed to said distal end portion, a needle adapted to obtain a blood sample from a patient with poor peripheral access for obtaining said sample through said needle.

* * * * *